US011517203B2

(12) United States Patent
Reifman et al.

(10) Patent No.: US 11,517,203 B2
(45) Date of Patent: Dec. 6, 2022

(54) REAL-TIME ESTIMATION OF HUMAN CORE BODY TEMPERATURE BASED ON NON-INVASIVE PHYSIOLOGICAL MEASUREMENTS

(71) Applicant: The Government of the United States, as Represented by the Secretary of the Army, Fort Detrick, MD (US)

(72) Inventors: Jaques Reifman, New Market, MD (US); Srinivas Laxminarayan, Frederick, MD (US); Vineet Rakesh, Frederick, MD (US); Sridhar Ramakrishnan, Frederick, MD (US); Jianbo Liu, Lexington, VA (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 623 days.

(21) Appl. No.: 16/327,846

(22) PCT Filed: Aug. 18, 2017

(86) PCT No.: PCT/US2017/047547
§ 371 (c)(1),
(2) Date: Feb. 24, 2019

(87) PCT Pub. No.: WO2018/039058
PCT Pub. Date: Mar. 1, 2018

(65) Prior Publication Data
US 2019/0192009 A1    Jun. 27, 2019

Related U.S. Application Data
(60) Provisional application No. 62/379,522, filed on Aug. 25, 2016.

(51) Int. Cl.
*A61B 5/01* (2006.01)
*H04L 41/5006* (2022.01)
(Continued)

(52) U.S. Cl.
CPC ............. *A61B 5/01* (2013.01); *A61B 5/024* (2013.01); *H04L 41/5006* (2013.01);
(Continued)

(58) Field of Classification Search
CPC ................. A61B 5/01; A61B 5/725
See application file for complete search history.

(56) References Cited

U.S. PATENT DOCUMENTS 4,883,063 A    11/1989  Bernard et al.
5,441,476 A *   8/1995  Kitado ................. A61M 21/00
                                              600/21
(Continued)

FOREIGN PATENT DOCUMENTS

CA    2650576 A1    10/2006
FR    2998158 A1     5/2014
(Continued)

OTHER PUBLICATIONS

Cuddy, John S. et al., "A reduced core to skin temperature gradient, not a critical core temperature, affects aerobic capacity in the heat," vol. 43, Jul. 2014, pp. 7-12.
(Continued)

*Primary Examiner* — Fabricio R Murillo Garcia
(74) *Attorney, Agent, or Firm* — Leigh Z. Callander

(57) ABSTRACT

An embodiment of the invention provides a method of estimating a body temperature of an individual where physiological data is received from at least one sensor 510. Environmental data is received and the physiological data and the environmental data are input into a model. The model generates an estimated body temperature and an
(Continued)

estimated physiological condition based on the physiological data and the environmental data. A processor 520 compares the estimated physiological condition to a measured physiological condition in the physiological data. A controller 530 modifies at least one parameter in the model when the difference between the estimated physiological condition and the measured physiological condition is above a threshold.

20 Claims, 7 Drawing Sheets

(51) Int. Cl.
| | | |
|---|---|---|
| *H04W 4/70* | (2018.01) | |
| *H04L 43/08* | (2022.01) | |
| *A61B 5/024* | (2006.01) | |
| *H04L 67/50* | (2022.01) | |
| *A61B 5/00* | (2006.01) | |
| *G16H 50/30* | (2018.01) | |
| *A61B 5/0205* | (2006.01) | |

(52) U.S. Cl.
CPC ............ *H04L 43/08* (2013.01); *H04L 67/535* (2022.05); *H04W 4/70* (2018.02); *A61B 5/0008* (2013.01); *A61B 5/02055* (2013.01); *A61B 5/681* (2013.01); *G16H 50/30* (2018.01)

(56) References Cited

U.S. PATENT DOCUMENTS

| | | | |
|---|---|---|---|
| 7,037,273 B2 | 5/2006 | Zhu et al. | |
| 7,251,454 B2 | 7/2007 | White | |
| 7,805,186 B2 | 9/2010 | Pulkkinen et al. | |
| 7,827,011 B2 | 11/2010 | Devaul et al. | |
| 7,883,463 B2 | 2/2011 | Sattler et al. | |
| 7,942,825 B2 | 5/2011 | Ranganathan et al. | |
| 8,204,786 B2 | 6/2012 | Leboeuf et al. | |
| 8,303,172 B2 | 11/2012 | Zei et al. | |
| 8,465,397 B2 | 6/2013 | Saalasti et al. | |
| 8,583,371 B1 * | 11/2013 | Goodzeit ............ | G01C 19/5776 701/501 |
| 8,936,552 B2 | 1/2015 | Kateraas et al. | |
| 9,204,798 B2 | 12/2015 | Proud | |
| 9,204,806 B2 | 12/2015 | Stivoric et al. | |
| 10,702,165 B2 | 7/2020 | Buller | |
| 2002/0009119 A1 | 1/2002 | Matthew et al. | |
| 2002/0165443 A1 | 11/2002 | Mori | |
| 2004/0034295 A1 | 2/2004 | Salganicoff et al. | |
| 2005/0113703 A1 | 5/2005 | Farringdon et al. | |
| 2007/0239038 A1 | 10/2007 | Nicolaescu et al. | |
| 2007/0295713 A1 | 12/2007 | Carlton-Foss | |
| 2008/0224866 A1 * | 9/2008 | Rehman ............. | G08B 13/2417 340/572.1 |
| 2008/0262320 A1 | 10/2008 | Schaefer et al. | |
| 2009/0069642 A1 | 3/2009 | Gao et al. | |
| 2009/0069647 A1 | 3/2009 | McNames et al. | |
| 2010/0081971 A1 * | 4/2010 | Allison ..................... | A61F 7/00 606/1 |
| 2010/0113894 A1 | 5/2010 | Padiy | |
| 2010/0280331 A1 | 11/2010 | Kaufman et al. | |
| 2011/0004072 A1 | 1/2011 | Fletcher et al. | |
| 2011/0144457 A1 | 6/2011 | Coulon | |
| 2011/0251495 A1 | 10/2011 | Province et al. | |
| 2011/0257542 A1 | 10/2011 | Russell et al. | |
| 2011/0288381 A1 | 11/2011 | Bartholomew et al. | |
| 2011/0301432 A1 | 12/2011 | Riley et al. | |
| 2012/0022336 A1 | 1/2012 | Teixeira et al. | |
| 2012/0078127 A1 * | 3/2012 | McDonald ............... | A61B 5/11 600/508 |
| 2012/0197584 A1 | 8/2012 | Coates | |
| 2013/0237772 A1 | 9/2013 | Pisani et al. | |
| 2013/0345978 A1 | 12/2013 | Lush et al. | |
| 2014/0180027 A1 * | 6/2014 | Buller ..................... | A61B 5/01 600/301 |
| 2014/0249434 A1 * | 9/2014 | Banet .................. | A61B 5/14551 600/485 |
| 2014/0343372 A1 | 11/2014 | Ahmed et al. | |
| 2014/0357960 A1 | 12/2014 | Phillips et al. | |
| 2015/0031964 A1 | 1/2015 | Bly et al. | |
| 2015/0106052 A1 | 4/2015 | Balakrishnan et al. | |
| 2015/0142332 A1 | 5/2015 | Jeon et al. | |
| 2016/0081629 A1 | 3/2016 | Rostalski et al. | |
| 2017/0071477 A1 | 3/2017 | Lin et al. | |
| 2017/0238811 A1 | 8/2017 | Buller et al. | |
| 2019/0029537 A1 | 1/2019 | Buller | |

FOREIGN PATENT DOCUMENTS

| | | |
|---|---|---|
| JP | 2005226902 A | 8/2005 |
| WO | 2009/034218 A | 3/2009 |
| WO | 2011032016 A1 | 3/2011 |
| WO | 2015/185927 A1 | 12/2015 |
| WO | 2017/181195 A1 | 10/2017 |
| WO | 2017/181196 A1 | 10/2017 |
| WO | 2020180454 A9 | 10/2020 |

OTHER PUBLICATIONS

Wright-Beatty, Heather E. et al., "Increased air velocity during exercise in the heat leads to equal reductions in hydration shifts and interleukin-6 with age," Jun. 19, 2014, vol. 114, Issue 10, pp. 2081-2092.

Al-Mukhaizeem, F., et al., "Comparison of temporal artery, rectal and esophageal core temperature in children: results of pilot study", Pediatric Child Health, Sep. 2004, pp. 461-465, vol. 9.

Bland, J. and Altman, D., "Statistical methods for assessing agreement between two methods of clinical measurements," Lancet, 1986, pp. 307-310, vol. 1.

Brauer, A., et al., "Determination of core body temperature. A comparison of esophogeal, bladder and rectal temperature: A comparison of esophageal, bladder and rectal temperature during postoperative rewarming" (translated title), Der Anaesthesist, Fall 1997, pp. 683-688, vol. 46.

Buller, MJ. et al., "Thermal work strain during Marine rifle squad operations in Afghanistan (Mar. 2010)," USARIEM Technical Report No. T11-02 (AD A501301), Mar. 2010, pp. 1-39.

Buller, Mark J, et al. "Estimation of Human Internal Temperature from Wearable Physiological Sensors." IAAI. 2010.

Buller, M.J. et al.; "Human thermoregulatory system state estimation using non-invasive physiological sensors," in Engineering in Medicine and Biology Society, EMBC, 2011 Annual International Conference of the IEEE, vol. No., pp. 3290-3293, Aug. 30 2011-Sep. 3 2011.

Buller, M.J. et al., "Estimation of human core temperature from sequential heart rate observations," Physiological Measurement, 2013, pp. 781-798, vol. 34.

Byrne, C. and Lim, C.L., "The ingestible telemetric body core temperature sensor: a review of validity and exercise applications," Br. J. Sport Med., 2007, pp. 126-133, vol. 41.

Cheuvront, Samuel et al., "Evaluation of the limits to accurate sweat loss prediction during prolonged exercise," Eur. J. Appl. Physiol., 2007, pp. 215-224, vol. 101.

Cuddy, JS et al., abstract for "Skin temperature and heart rate can be used to estimate physiological strain during exercise in the heart in a cohort of fit and until males," Association of Military Surgeons of the U.S., Mil Med., Jul. 2013.

Degroot, David W. et al., "Prediction Models for Core Temperature During Heat Stress Vary with Exercise Intensity," Medicine & Science in Sports & Exercise, May 2007, p. S436, vol. 39, issue 5.

Degroot, David W. et al., "Validation of the ICDA model for predicting body core temperature," Medical & Science in Sports & Exercise, May 2008, p. S367, vol. 40, issue S.

Fiala, Dusan et al.,"Computer prediction of human thermoregulatory and temperature responses to a wide range of environmental conditions," International Journal Biometeorol, 2001, pp. 143-159, vol. 45.

(56) References Cited

OTHER PUBLICATIONS

Fick, Adolph, "On liquid diffusions," Journal of Membrane Science, 1995, pp. 30-39, vol. 10.
Fox, R.H. et al., "A new method for monitoring deep body temperature from the skin surface," Clinical Science, 1973, pp. 81-86, vol. 44.
Frank, A. et al., "The cumulative heat strain index—a novel approach to assess the physiological strain induced by exercise heat stress," Eur. J. Appl. Physiol, 2001, pp. 527-532, vol. 84.
Grubbs, Frank E., "Procedures for detecting outlying observations in samples," AD-781 499, BRL Report No. 1713, Apr. 1974, pp. 1-53.
Gunga, Hanns-Christian et al., "A non-invasive device to continuously determine heat strain in humans," Journal of Thermal Biology, 2008, pp. 297-307, vol. 33.
Gunga, H.C., et al., "The double sensor—a non invasive device to continuously monitor core temperature in humans on earth and in space," Respir. Physiol, Neurobiology, 2009, pp. S63-S68, vol. 169S.
Havenith, George, "Individualized model of human thermoregulation for the simulation of heat stress response," J. Appl. Physiol., 2001, pp. 1943-1954, vol. 90.
Sargent II, Frederick et al., "Physiological variability in young men," Physiological Measurements of Metabolic Functions, ed. CF Consolazio, RE Johnson and LJ Pecora, 1963, pp. 453-480, New York: McGraw-Hill.
Kalman, R.E., "A New Approach to Linear Filtering and Prediction Problems," Journal of Basic Engineering, Mar. 1960, pp. 35-45, vol. 82.
Karp, Jason R., "Heart Rate Training for Improved Running Performance," www.coachr.org/heart_rate_training_for_improvement.htm., printed on Mar. 29, 2016.
Kenefick, Robert W. et al., "DEET insect repellent: effects on thermoregulatory sweating and physiological strain," Eur. J. Appl. Physiol., 2011, pp. 3061-3068, vol. 111.
Kraning, Kenneth K., "A mechanistic computer simulation of human work in heat that account for physical and physiological effects of clothing, aerobic fitness and progressive dehydration," Journal of Thermal Biology, 1997, pp. 331-342, vol. 22, No. 415.
Latzka, William A. et al., "Hyperhydration: thermoregualtory effects during compensable exercise heat stress," J. Appl. Physiol., 1997, pp. 860-866, vol. 83.
Latzka, William A. et al., "Hyperhydration: tolerance and cardiovascular effects during uncompensible exercise heat stress," J. Appl. Physiol., 1998, pp. 1858-1864, vol. 84.
Lee, Jason K.W. et al., "Thermoregulation, pacing and fluid balance during mass participation distance running in a warm and humid environment," Eur. Jour. Appl. Physiol., 2010, pp. 887-898, vol. 109.
Lefrant, J.Y. et al., "Temperature measurement in intensive care patients: comparison of urinary bladder, oesophageal, rectal, axillary, and inguinal methods versus pulmonary artery core method," Intensive Care Med., 2003, pp. 414-418, vol. 29.
Lim, Chin Leong et al., "Human Thermoregulation and Measurement of Body Temperature in Exercise and Clinical Settings," Annals Academy of Medicine, Apr. 2008, pp. 47-53, vol. 37, Singapore.
Montain, Scott J. et al., "Influence of graded dehydration on hyperthermia and cardiovascular drift during exercise," J. Appl. Physiol., 1992, pp. 1340-1350, vol. 73.
Moran, Daniel S. et al., "A physiological strain index to evaluate heat stress," American Journal of Physiological Regulation Integr. Comp. Physiol., 1998, pp. R129-R134, vol. 275.
Niedermann, Reto et al., "Prediction of human core body temperature using non-invasive measurement methods," International Journal of Biometeorology, published online Jun. 13, 2013, pp. 1-9.
Orderud, Fredrik, "Comparison of Kalman Filter Estimation Approaches for State Space Models with Nonlinear Measurements," In. Proc. of Scandinavian Conference on Simulation and Modeling, pp. 1-8, 2005.

Sawka, Michael N. et al., "Chapter 26 Physiological Systems and Their Responses to Conditions of Heat and Cold," ACSM's Advanced Exercise Physiology, ed. CM Tipton, MN Sawka, CA Tate, and RL Terjung, pp. 535-563, Williams & Wilkins, New York.
Steck, Luke N. et al., "Non-invasive measurement of the human core temperature," International Journal of Heat and Mass Transfer, 2011, pp. 975-982, vol. 54.
Teunissen, LPJ et al., "Non-invasive continuous core temperature measurement by zero heat flux," Physiological Measurement, 2011, pp. 559-570, vol. 32.
Welch, Greg et al., "An introduction to the Kalman Filter," Technical Report TR 95-041, Department of Computer Science, 2001, pp. 19-29, University of North Carolina at Chapel Hill, NC.
Yamakage, Michiaki et al., "Evaluation of newly developed monitor of deep body temperature," Journal of Anesthesia, 2002, pp. 354-357, vol. 16.
Yokota, Miyo et al., "Thermoregulatory model to predict physiological status from ambient environment and heart rate," Computers in Biology Medicine and Medicine, 2008, pp. 1187-1193, vol. 38.
Espacenet, English abstract for FR2998158 A1, printed on Mar. 21, 2016.
Espacenet, English abstract for JP2005226902 A, printed on Mar. 21, 2016.
Buller, Mark J. "Human Thermal-Work Strain Performance Optimization from Wearable Physiological Sensors." Dec. 31, 2015. https://cs.brown.edu/research/pubs/theses/phd/2015/buller.pdf, pp. 1-193.
Baratchi, Mitra, et al., "Towards Decisive Garments for Heat Stress Risk Detection," UBICOMP/ISWC '16 Adjunct, Sep. 12-16, 2016, pp. 1-6.
Richmond, Victoria L., et al., "Prediction of Core Body Temperature from Multiple Variables," The Annuals of Occupational Hygiene, 2015, pp. 1-11.
Seng, Kok-Yong, et al., "Nonlinear mixed effects modelling for the analysis of longitudinal body core temperature data in healthy volunteers," Physiological Measurement, vol. 37, Mar. 10, 2016, pp. 485-502.
U.S. Patent and Trademark Office, Written Opinion for PCT App. No. PCT/US2017/047547, dated Oct. 25, 2017.
U.S. Patent and Trademark Office, International Search Report for PCT App. No. PCT/US2017/047547, dated Oct. 25, 2017.
Bulut, Yalcin, et al., "Process and measurement noise estimation for kalman filtering," Structural Dynamics, Conf Proc Soc Exp Meeh Series 3: 375-386, 2011.
Ozaki, T. et al., The local linearization filter with application to nonlinear system identifications, Proc. first US/Japan Conf Frontiers Stat Modeling: An Informational Approach, Springer, pp. 217-240, 1994.
Belval, Luke N., "Thermoregulatory Responses of Runners following a Warm-Weather Road Race," University Scholar Projects, https://opencommons.uconn.edu/usp_projects/7, Spring 2014, pp. 1-36.
Cuddy, John S., et al., "Skin Temperature and Heart Rate Can Be Used to Estimate Physiological Strain During Exercise in the Heat in a Cohort of Fit and Unfit Males," Military Medicine, vol. 178, Jul. 2013, pp. e841-e847.
Ely, Brett R., "Evidence against a 40C core temperature threshold for fatigue in humans," Journal of Applied Physiology, vol. 107, Aug. 27, 2009, pp. 1519-1525.
Esteve-Lanao, Jonathan, et al., "How Do Humans Control Physiological Strain during Strenuous Endurance Excercise?," PLoS ONE, vol. 3, No. 8, https://doi.org/10.1371/journal.pone.0002943., Aug. 13, 2008, pp. 1-11.
Pandolf, Kent B., "Convergence of Skin and Rectal Temperatures as a Criterion for Heat Tolerance," Aviation, Space, and Environmental Medicine, vol. 49, Sep. 1978, pp. 1095-1101.
Pokora, Ilona, et al., "Application of A Physiological Strain Index in Evaluating Responses to Exercise Stress—A Comparison Between Endurance and High Intensity Intermittent Trained Athletes," Journal Human Kinetics, vol. 50, Apr. 13, 2016, pp. 103-114.

(56) References Cited

OTHER PUBLICATIONS

Varela, Manuel, et al., "Holter Monitoring of Central and Peripheral Temperature: Possible uses and Feasibility Study in Outpatient Settings," Journal of Clinical Monitoring and Computing, vol. 23, May 27, 2009, pp. 209-216.

Wan, Margaret, "Assessment of Occupational Heat Strain," Scholar Commons, Graduate Theses and Dissertations, http://scholarcommons.usf edu/etd/2745, Jul. 17, 2016, pp. 1-66.

Chen, Chi-Tsong, "Linear System Theory and Design," 3rd ed. Oxford, NY: Oxford University Press, 1999, pp. 106-111.

Sawka, Michael N., et al., "Intergrated Physiological Mechanisms of Exercise Performance, Adaptation, and Maladaptation to Heat Stress," Comprehensive Physiology, comprehensivephysiology.com, Oct. 2011, pp. 1883-1928, vol. 1.

Buller, Mark J., et al., "Real-time Core Body Temperature Estimation from Heart Rate for First Responders Wearing Different Levels of Personal Protective Equipment", Ergonomics, http://dx.doi.org/10.1080/00140139.2015.1036792, 2015, pp. 1-12.

Fiala, Dusan, et al., "A Computer Model of Human Thermoregulation for a Wide Range of Environmental Conditions: The Passive System", Journal of Applied Physiology, Nov. 1, 1999, pp. 1957-1972, vol. 87, Issue 5.

Gribok, Andrei, et al., "Regularization of Body Core Temperature Prediction during Physical Activity", Proceedings of the 28th IEEE EMBS Annual International Conference, New York, NY, Aug. 30-Sep. 3, 2006, pp. 459-463.

Gunga, H. C., et al., "The Double Sensor—A Non-Invasive Device to Continuously Monitor Core Temperature in Humans on Earth and in Space," Respiratory Physiology & Neurobiology, Oct. 2009, pp. S63-S68, vol. 169, Supplement.

Laxminarayan, Srinivas, et al., "Preventing Heat Injuries by Predicting Individualized Human Core Temperature", Proceedings of the HFM-254 Symposium on Health Surveillance and Informatics in Missions: Multidisciplinary Approaches and Perspectives, STO-MP-HFM-254, Oct. 12-14, 2015, pp. 21-1 to 21-11.

Oleng, Nicholas, et al., "Hybrid Approaches to Physiologic Modeling and Prediction", Proceedings of the Biomonitoring for Physiological and Cognitive Performance during Military Operations—International Society for Optical Engineering, Mar. 31-Apr. 1, 2005, pp. 193-203, vol. 5797.

Potter, Adam W., et al., "Mathematical Prediction of Core Body Temperature from Environment, Activity, and Clothing: The Heat Strain Decision Aid (HSDA)", Journal of Thermal Biology, 2017, pp. 78-85, vol. 64.

Richmond, Victoria L., et al., "Prediction of Core Body Temperature from Multiple Variables", Occupational Hygiene Society, Aug. 12, 2015, pp. 1168-1178, vol. 59, No. 9.

Wilkinson, David M, et al., "The Effect of Cool Water Ingestion on Gastrointestinal Pill Temperature", Medicine and Science in Sports and Exercise, 2008, pp. 523-528, vol. 40, No. 3.

\* cited by examiner

REAL-TIME ESTIMATION OF HUMAN CORE BODY TEMPERATURE BASED ON NON-INVASIVE PHYSIOLOGICAL MEASUREMENTS

This patent application is the National Stage Entry of International Application No. PCT/US2017/047547, filed on Aug. 18, 2017, which claimed the benefit of and priority to U.S. Patent Application No. 62/379,522 filed on Aug. 25, 2016 in the U.S. Patent and Trademark Office, which are hereby incorporated by reference in its entirety.

I. FIELD OF INVENTION

The present invention relates to systems, methods, and computer program products for real-time estimation of human core body temperature based on non-invasive physiological measurements. Heat injury is a problem for the U.S. Armed Forces, especially during deployments to localities with hot and humid climates, and trends show the number of heat injury cases to be on the rise each year. From 2006 through 2010, there were 2887 heat injuries across the services, including 311 cases of heat stroke. Nevertheless, to date, there are no practical solutions to alert service members of an impending heat injury and help prevent them.

II. SUMMARY OF THE INVENTION

An embodiment of the invention provides a method of estimating a body temperature of an individual where physiological data is received from at least one sensor. Environmental data is received and the physiological data and the environmental data are input into a model. The model generates an estimated body temperature and an estimated physiological condition based on the physiological data and the environmental data. A processor compares the estimated physiological condition to a measured physiological condition in the physiological data. A controller modifies at least one parameter in the model when the difference between the estimated physiological condition and the measured physiological condition is above a threshold.

III. BRIEF DESCRIPTION OF THE DRAWINGS

The present invention is described with reference to the accompanying drawings. In the drawings, like reference numbers indicate identical or functionally similar elements.

IV. DETAILED DESCRIPTION

Non-limiting embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system that determines an individual's core body temperature based on noninvasive measurements of the individual's heart rate, activity, and skin temperature, as well as measurements of two environmental variables, such as ambient temperature and relative humidity. A fitness-tracking device, such as an electronic wristband or watch, can collect the individual's non-invasive physiological data and wirelessly transmit the data to a mobile computing platform (e.g., smartphone, tablet computer). In at least one embodiment, the mobile computing platform is on the fitness-tracking device.

Figure 1:
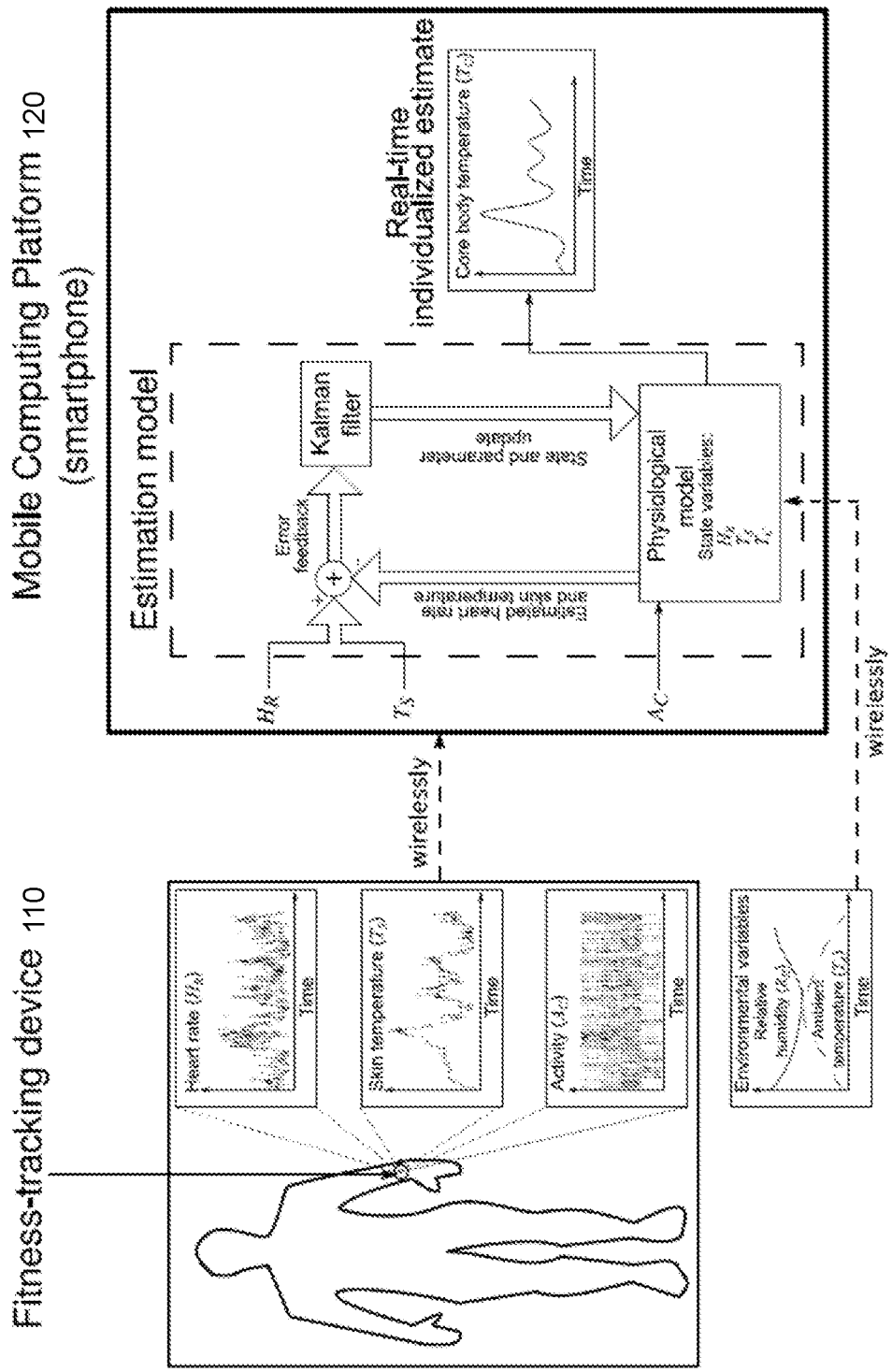
FIG. 1 illustrates a system for real-time individualized core body temperature estimation according to an embodiment of the invention.

As illustrated in FIG. 1, physiological data can be captured by a fitness-tracking device 110 and input into an estimation model in a mobile computing platform 120, where the estimation model can use the physiological data to adapt the model parameters to the individual and provides individualized core body temperature estimates in real time. In at least one embodiment, the fitness-tracking device 110 includes a chest strap or a wrist watch, which continually collects an individual's heart rate, activity (e.g., via a 3 axis accelerometer), and skin temperature.

FIG. 1 illustrates a schematic representation of a system for real-time individualized core body temperature estimation. Data can include the measured heart rate (HR), skin temperature (TS), and activity (AC) from a wrist-worn fitness-tracking and measurements of two environmental variables (e.g., ambient temperature (TA) and relative humidity (RH)) can be wirelessly transmitted to the mobile computing platform. The activity (accelerometer) data and environmental factors can drive the mathematical model, while HR and TS data can be used to improve the quality of the core body temperature (TC) estimates via a Kalman filter algorithm. This process can be repeated every minute (or at another sampling rate) after each measurement of HR, AC, and TS.

The core body temperature estimation mathematical model can include a physiological mathematical model and a Kalman filter algorithm. These two elements can feed information to one another to "learn" the individual's response to environmental and exertional heat stresses, and produce an individualized estimation of core body temperature in real time (FIG. 1). The mathematical model can describe the heat balance between the body core and the external environment in terms of three equations that relate physical activity to heart rate, heart rate to core body temperature, and core body temperature to skin temperature. First, the mathematical model can use the current activity level of the subject, as measured by an accelerometer, and hourly (or another frequency) measurements of ambient temperature and relative humidity to estimate the heart rate, skin temperature, and core body temperature of the subject.

In at least one embodiment, the Kalman filter considers the errors between the estimates provided by the mathematical model and the actual measured heart rate and skin temperature of the individual, and can provide corrections by adjusting up to seven parameters in the mathematical model. In at least one embodiment, the seven parameters, which may be continually adjusted and updated, account for features such as the rate of heat gain due to metabolic activity, the rate of convective heat loss or gain from the skin surface to the environment, and the rate of heat loss to the environment due to sweat evaporation, among others. The algorithm can repeat this procedure after measurements of heart rate, activity, and skin temperature every minute to update the model parameters, individualize the model, and provide new estimates of core body temperature that reflect the subject's physiological response to environmental and exertional heat stress.

Figure 2:
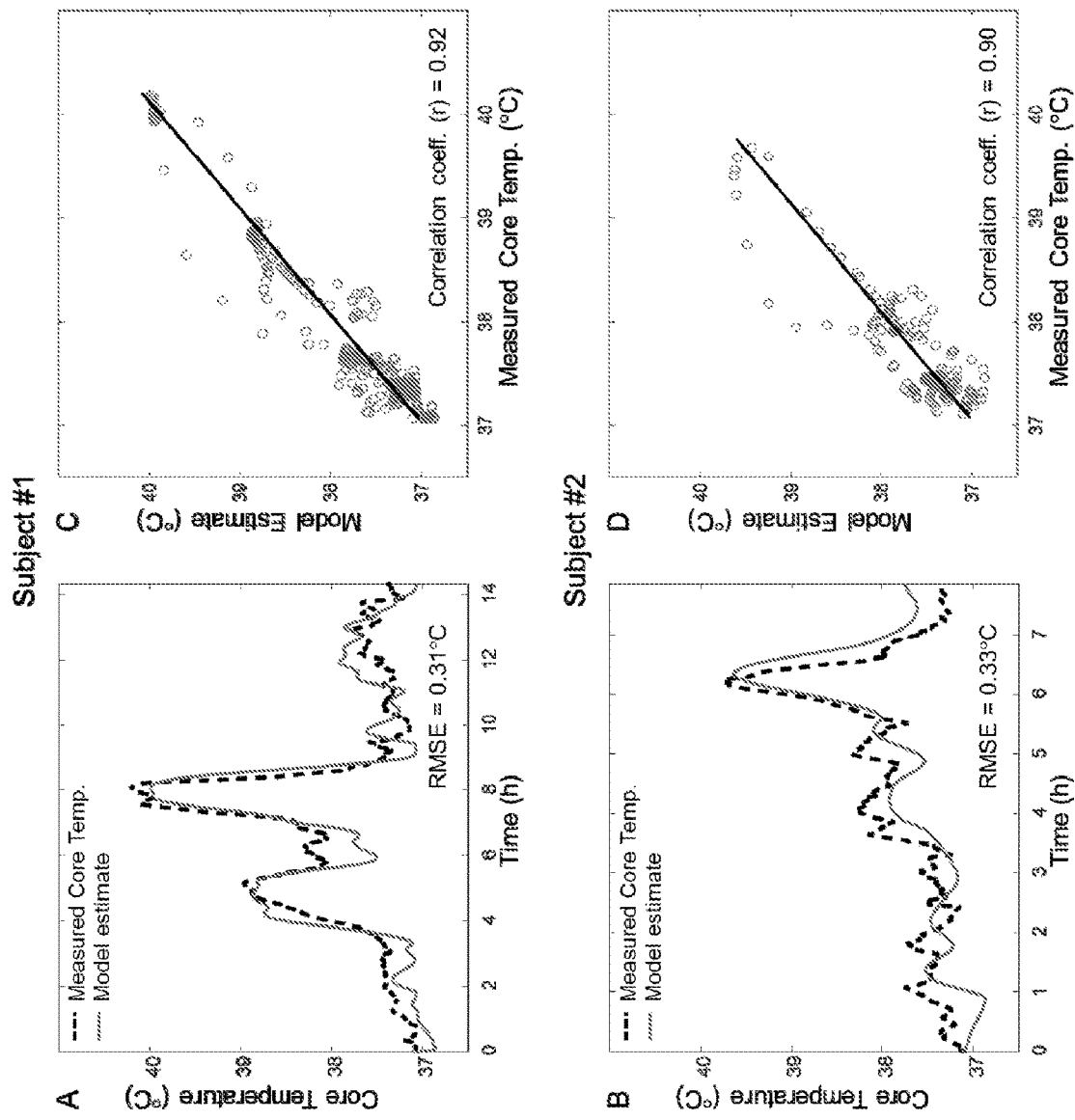
FIGS. 2A-2D are graphs illustrating the performance of the individualized core body temperature model according to an embodiment of the invention.

FIGS. 2A-2D show the performance of the individualized core body temperature model. Specifically, FIGS. 2A-2D illustrate the model-estimated and measured (via an ingestible pill) core body temperature for two subjects whose temperature exceeded 39° C. FIGS. 2A-2D also show the correlation (r) between the measured and estimated core body temperatures for the corresponding subjects (r ranged from 0.90 to 0.92). FIGS. 2A-2B illustrate the core body temperatures of two study subjects over 12 hours of activity as measured by a thermometer radio pill (dashed lines) and estimated by the individualized model (solid lines). FIGS. 2C-2D show the correlation between measured and model-estimated core body temperatures for both subjects (RMSE=root mean squared error).

In contrast to an invasive, ingestible thermometer pill, which does not offer a practical means to continually monitor a large number of individuals, the system is based on non-invasive physiological measurements, which may be available through use of a range of fitness-tracking devices. Furthermore, unlike data-driven mathematical algorithms that may not capture an individual's underlying physiology and may only provide the response of an average individual, the system can implicitly account for subject-specific variations in thermoregulatory responses. This can provide core body temperature estimates that are individualized to the specific person. This ability to continually learn an individual's response to heat stress can allow for a more accurate and broader applicability of the model. In addition, because the model can rely on multiple physiological measurements, it is less susceptible to the failure of any one sensor. For instance, if the accelerometer fails, the model can still rely on heart rate and skin temperature measurements.

In at least one embodiment, the system can also be used to predict core body temperature (e.g., 20 minutes in advance) and provide ample time to intervene and prevent an impending heat injury. This can be achieved by coupling a series of estimated core body temperatures with a predictive model in the development of a real-time, heat-injury warning system.

Figure 3:
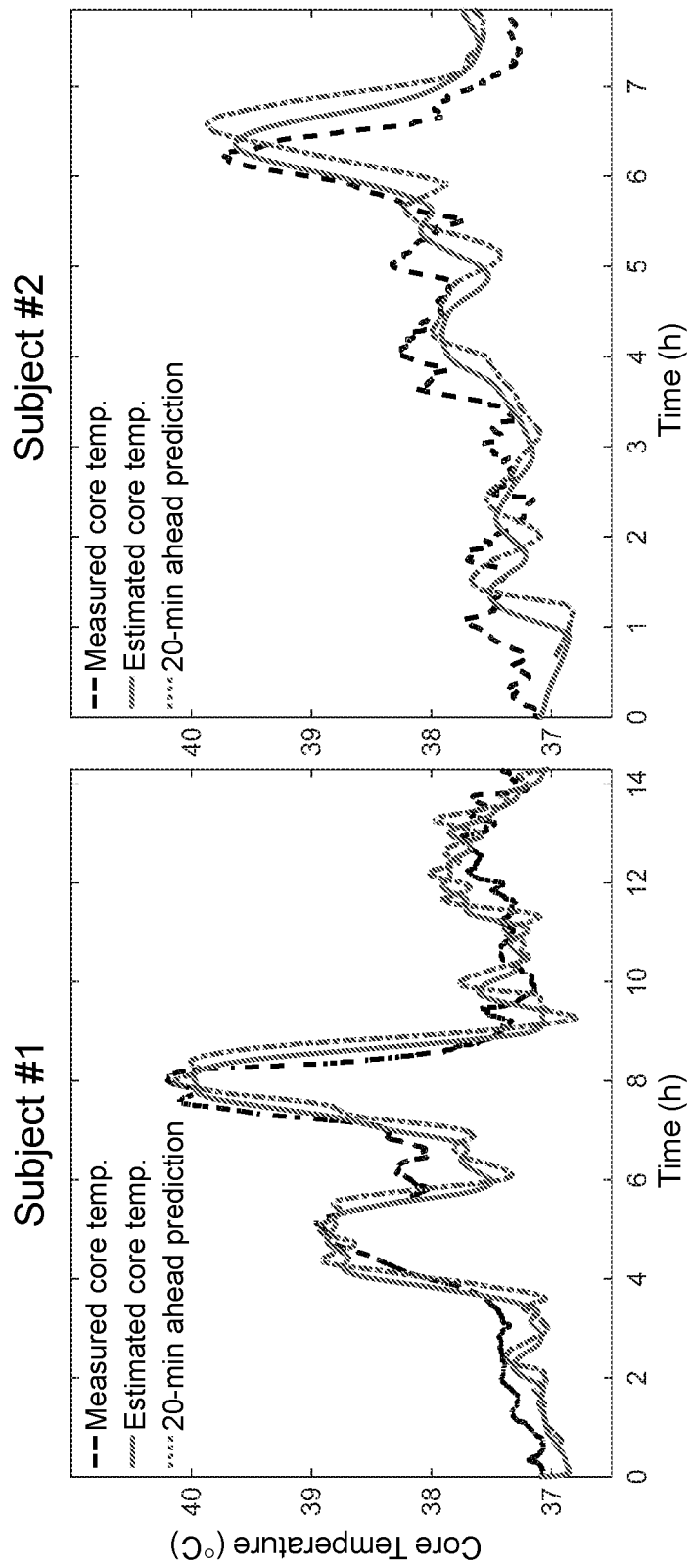
FIG. 3 are graphs illustrating core temperature predictions according to an embodiment of the invention.

Core body temperature can be predicted using an autoregressive (AR) model. Given core body temperature values $y_{n-i}$ estimated, for example, every 1 minute, where n is the current discrete time index and i=0, 1, . . . , m−1, an AR model of order m can predict temperature $\hat{y}_{n+1}$, at time point n+1, through a linear combination of the antecedent core temperature estimates as follows:

$$\hat{y}_{n+1} = \sum_{i=0}^{m-1} b_i y_{n-1}$$

where b denotes the vector of m AR coefficients. In at least one embodiment, it is assumed that activity, heart rate, and skin temperature stay the same. To make predictions M time steps ahead, one can iteratively use the above equation M times, substituting the unobserved temperatures at n≥n+1 in the summation by their corresponding predicted values. The order m of the model can specify the required initial waiting period for which temperature values need to be estimated before real-time predictions can be made. FIG. 3 shows 20-minute-ahead predictions for the same two subjects illustrated in FIG. 2. In addition to the predictions, FIG. 3 also shows the measured and estimated core temperature values.

At least one embodiment of the invention provides a system and method for real-time, non-invasive estimation of core body temperature using an estimation model based on phenomenological and conservation of energy principles. The system can continually adapt the estimation model to an individual based on the individual's non-invasive physiological measurements. The system can automatically account for individual-specific variations in thermoregulatory responses due to acclimation and reactions to exogenous factors, such as clothing and environmental conditions.

Figure 4:
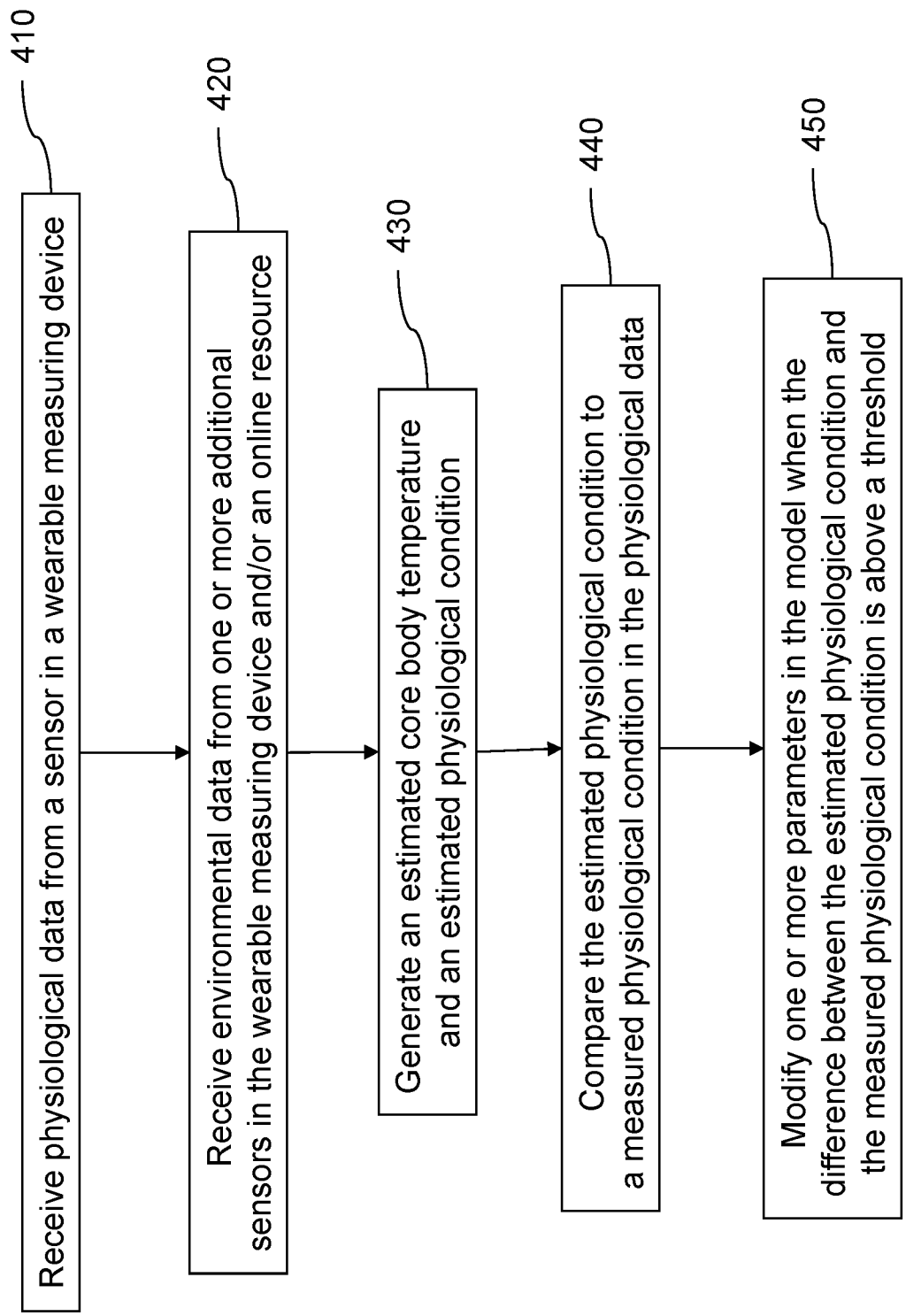
FIG. 4 is a block diagram illustrating a method for estimating a body temperature of an individual according to an embodiment of the invention.

FIG. 4 illustrating a method for estimating a body temperature of an individual according to an embodiment of the invention (e.g., using the system 400). A processor can receive physiological data from a sensor in a wearable measuring device (a wearable accelerometer) 410. The processor can be in the wearable measuring device or in wireless communication with the wearable measuring device. The physiological data can include the heart rate, the skin temperature, and/or activity data of the individual. The physiological data can be from different body locations. The activity data can include the running speed of the individual and/or an activity score of the individual (e.g., low, moderate, high, and very high). In at least one embodiment, the processor receives the 3-D body acceleration of the individual from the wearable measuring device and maps the body acceleration into Metabolic Equivalent (MET, amount of energy burned during exercise) units to determine the activity score of the individual.

The processor can also receive environmental data (ambient temperature and/or humidity) from one or more additional sensors in the wearable measuring device and/or an online resource (e.g., weather website) 420. In at least one embodiment, the processor determines the location of the sensor with a global positioning system (GPS) device in the measuring device and queries an online resource with the location of the sensor to retrieve the environmental data.

The processor uses the received physiological data and the environmental data a model, and the model generates an estimated core body temperature and an estimated physiological condition (e.g., heart rate and/or skin temperature) based on the physiological data and the environmental data 430. In at least one embodiment, the physiological data and/or the environmental data are constantly measured such that the estimating of the core body temperature of the individual is performed in real time. The model can include a physiological mathematical model and a Kalman filter that feed information to one another to learn the individual's response to environmental and exertional heat stresses.

More specifically, the physiological mathematical model can include a first equation that relates physical activity to heart rate, a second equation that relates heart rate to core body temperature, and a third equation that relates core body temperature to skin temperature. The first mathematical equation above can be motivated by the observation that an increase in physical activity $A_C$ leads to a rapid increase in heart rate $H_R$, followed by an exponential decay when $A_C$ decreases. In at least one embodiment, this is mathematically represented by:

$$\frac{d\Delta H_R}{dt} = -\alpha_1 \Delta H_R + \beta A_C^4$$

where $\Delta H_R$ denotes the change in heart rate from a resting state $H_{R0}$ (i.e., $\Delta H_R = H_R - H_{R0}$), $\alpha_1$ denotes the rate constant for $H_R$, and $\beta$ represents the gain in $H_R$ due to physical activity. In at least one embodiment, $A_C^4$ is used to ensure good separation of the $H_R$ due to different activity levels; a feature noted during data analysis, e.g., $A_C=2$ (moderate activity) must lead to a larger increase in $H_R$ when compared to $A_C=1$ (light activity). $H_{R0}$ can be set as the mean of the measured $H_R$ for the initial 5 minutes of the data (~80 beats/min) representing light activity levels.

In at least one embodiment of the invention, the second and third equations in the model represent the core temperature $T_C$ and skin temperature $T_S$, respectively, at the current time, as:

$$\frac{d\Delta T_C}{dt} = -\alpha_2 \Delta T_C + \gamma_1 \Delta H_R - \gamma_2 (T_C - T_S)$$

$$\frac{d\Delta T_S}{dt} = -\alpha_3 (T_S - T_A) - \alpha_4 (P_S - P_A) + \gamma_2 (T_C - T_S)$$

where $\Delta T_C = T_C - T_{C0}$ and $\Delta T_S = T_S - T_{S0}$, with $T_{C0}$ and $T_{S0}$ denoting the initial core and skin temperatures, respectively, $P_S$ denotes the vapor pressure of water for $T_S$, and $P_A$ represents the vapor pressure of water due to the heat index perceived by humans at a given ambient temperature $T_A$ and relative humidity $R_H$. $T_{S0}$ can be set as the mean of the measured $T_S$ during the initial 5 minutes and $T_{C0}$ to 37° C. In the second equation of the model, $\alpha_2$ can denote the thermoregulatory rate constant of $T_C$, $\gamma_1$ can denote the rate of heat gain due to metabolic activity ($H_R$), and $\gamma_2$ can represent the rate of heat loss/gain from the core to the skin. In the third equation of the model, $\alpha_3$ can denote the rate of convective heat loss/gain from the skin to the environment and $\alpha_4$ can denote the rate of heat loss to the environment due to sweat evaporation. Thus, the mathematical model consists of three states ($\Delta H_R$, $\Delta T_C$, and $\Delta T_S$ corresponding to the three equations of the model) and seven unknown parameters ($\alpha_1$, $\alpha_2$, $\beta$, $\gamma_1$, $\gamma_2$, $\alpha_3$, and $\alpha_4$).

The processor can compare the estimated physiological condition to a measured physiological condition in the physiological data 440. For example, the estimated physiological condition includes an estimated heart rate and an estimated skin temperature; and the measured physiological condition includes a measured heart rate and a measured skin temperature. The measured heart rate and the measured skin temperature can be used to customize the model to the individual via a Kalman filter algorithm.

A controller connected to the processor can modify one or more parameters in the model when the difference between the estimated physiological condition and the measured physiological condition is above a threshold 450. The modifying of the parameter(s) in the model can include modifying a rate constant for the heart rate signal ($\alpha_1$), a thermoregulatory rate constant for the core temperature signal ($\alpha_2$), a rate of convective heat loss/gain from the skin to the environment ($\alpha_3$), a rate of heat loss to the environment due to sweat evaporation ($\alpha_4$), a gain in heart rate due to physical activity ($\beta$), a rate of heat gain due to metabolic activity ($\gamma_1$), and/or a rate of heat loss/gain from the core to the skin ($\gamma_2$).

The model can use the physiological data and the environmental data to learn a physiological response of the individual and automatically adjust parameter(s) in the model to produce an individualized model. The model can include a Kalman filter where the comparing of the estimated physiological condition to the measured physiological condition and the modifying of the at least one parameter in the model is performed by the Kalman filter. In at least one embodiment, a communications device such as a transmitter or a transceiver connected to the sensor sends data from the sensor to an external computing device (e.g., smartphone, tablet computer), where the processor and the controller are on the external computing device. The processor can predict a future core body temperature of the individual based on the estimated core body temperature and at least one additional estimated core body temperature, where the estimated core body temperature(s) are generated after the parameter(s) in the model are modified.

Figure 5:
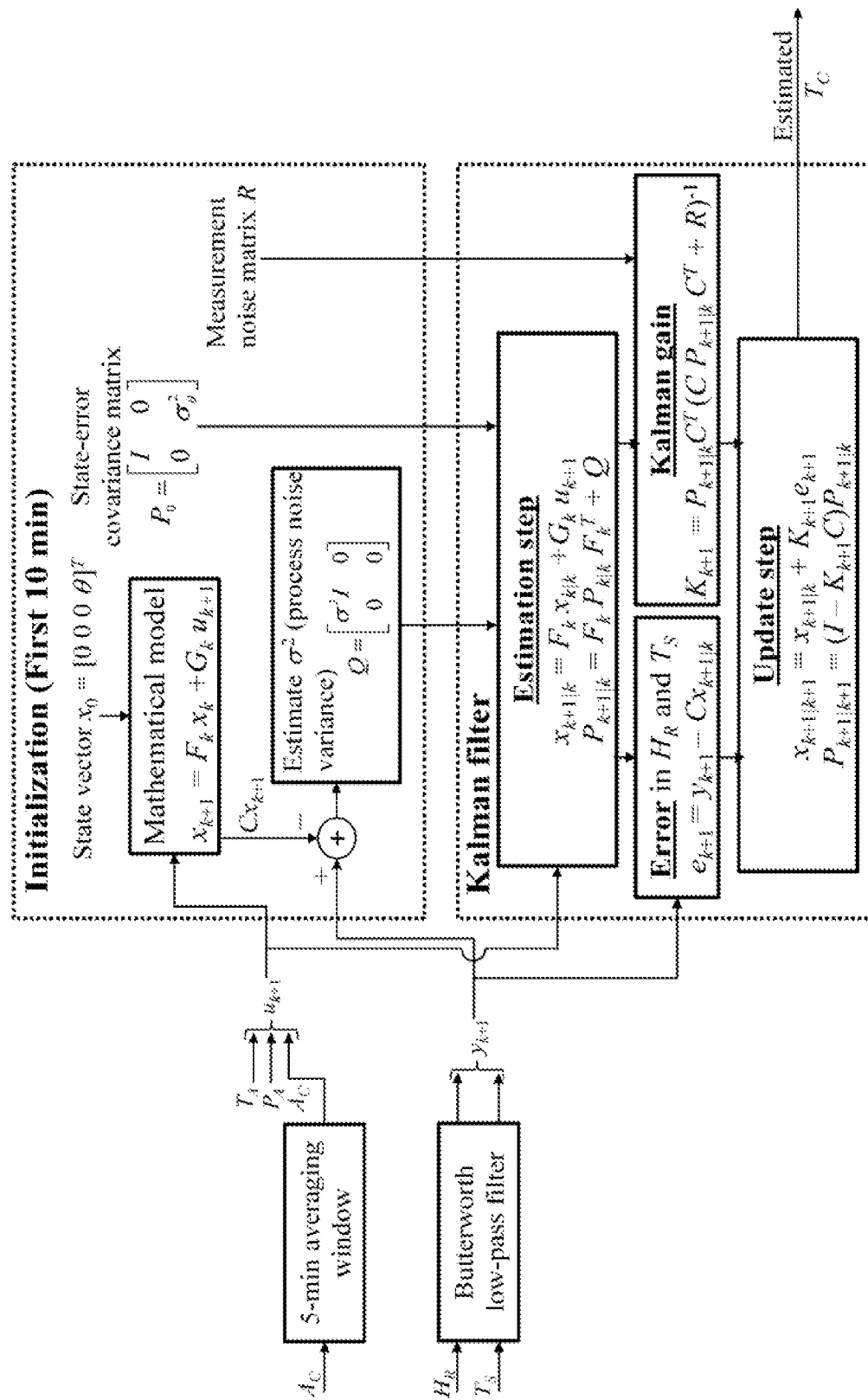
FIG. 5 is a flow diagram illustrating the initialization and subsequent steps of the Kalman filter algorithm for real-time core body temperature estimation according to an embodiment of the invention.

FIG. 5 is a flow diagram illustrating the initialization and subsequent steps of the Kalman filter algorithm for real-time core body temperature ($T_C$) estimation. The algorithm can be initialized with $\theta$, $\sigma_\theta^2$, the $H_R$ and $T_S$ measurement noise variances (matrix R), and the process noise variance $\sigma^2$ estimated from the first 10 minutes of data for each subject. After initialization, the algorithm can use $u_{k+1}$ to drive the mathematical model to estimate $H_R$ and $T_S$ (Estimation step). Then, by scaling the error $e_{k+1}$ between the filtered measurements and the model-estimated $H_R$ and $T_S$ by the Kalman gain $K_{k+1}$, the algorithm can update the model parameters and the $T_C$ estimates at each time index (Update step) until the end of the measured time-series data.

To implement the Kalman filter algorithm, the continuous-time nonlinear model (i.e., the three previous equations) can be converted into a discrete linear model. In at least one embodiment, to discretize the model, the three equations are of the form $\dot{x}=f(x, u)$, with states $x=[\Delta H_R \ \Delta T_C \ \Delta T_S \theta]^T$, where $\theta=\phi^{1/2}$ (to ensure non-negative parameter values), with $\phi$ representing the vector of the six adjustable model parameters, $f(\cdot)$ denoting a set of nonlinear functions, and $u=[A_C^4 \ T_A \ P_A]^T$. Subsequent steps can include computing the Jacobian of $f(x, u)$ [1] and discretizing the results to obtain a linear time-varying model [2]. In at least one embodiment, the discrete model has state equations $x_{k+1}=F_k x_k \ G_k \ u_{k+1}$ and output equations $y_k=C \ x_k + y_0$, where $F_k$ and $G_k$ denote the discrete linearized state-transition and input matrices, respectively, obtained at each time index k, C denotes the matrix that outputs the estimated $\Delta H_R$ and $\Delta T_S$ signals, and $y_0=[H_{R0} \ T_{S0}]^T$ represents the vector of the mean values of $H_R$ and $T_S$ from the initial 10 minutes of data, which are used to initialize the model.

The flowchart in FIG. 5 depicts the initialization of, and sequence of steps involved in, the Kalman filter algorithm according to an embodiment of the invention. In at least one embodiment, the algorithm is initialized with parameter values ($\theta$) obtained from previously published studies, as described above (represented in the initial state vector $x_0$), their corresponding variances $\sigma_\theta^2$ (represented in the initial state-error covariance matrix $P_0$), the noise variances of the $H_R$ and $T_S$ measurements obtained from the first 10 minutes of data (represented in matrix R), and a measure of the systemic uncertainty ($\sigma^2$ in matrix Q) between the mathematical model estimates and a subject's data. Using each subject's first 10 minutes of data, $\sigma^2$ can be estimated by first filtering the measured $H_R$ and $T_S$ in real time, using a second-order, causal low-pass Butterworth filter with a cut-off frequency of 3.3 mHz, to reject noise while preserving the frequency band that overlaps with the measured $T_C$. A 5-minute moving average of the measured $A_C$, the measured $T_A$, and $P_A$ (computed from the measured $T_A$ and $R_H$) can be used to drive the mathematical model. The error between the filtered $H_R$ and $T_S$ data and the corresponding model estimates can be computed, which can be linearly related to the systemic uncertainty in the model states. This can allow the estimation of $\sigma^2$ by solving the resulting linear least-squares problem [3].

After initialization, the Kalman filter algorithm can proceed in the following manner: at each 15-s discrete time interval, the algorithm can use a 5-minute moving average of the measured (or computed) $A_C$, the measured $T_A$, the $P_A$ at the present time index k+1, and the model parameters obtained up to time index k to estimate the model states $x_{k+1|k}$ (FIG. 5, Estimation step). In the estimation step, the algorithm can also estimate the state-error covariance matrix $P_{k+1|k}$, using the model parameters up to time index k and the process noise matrix Q. Subsequently, the algorithm can compute the Kalman gain $K_{k+1}$ and use the error $e_{k+1}$ between the filtered measurements ($y_{k+1}$) and the estimated $H_R$ and $T_S$ ($Cx_{k+1|k}$) to update the $T_C$ estimate (an element of the state vector $x_{k+1|k+1}$), the model parameters, and the state-error covariance matrix $P_{k+1|k+1}$ (FIG. 5, Update step). In situations where $H_R$ or $T_S$ measurements were temporarily unavailable (i.e., missing measurements), it can be assumed that the noise characteristics of the error at time point k+1 would not be drastically different from the previous time point k, and hence set $e_{k+1}$ to $e_k$ in the Update step. The algorithm can repeat this procedure for each time step until the end of the time-series data.

Figure 6:
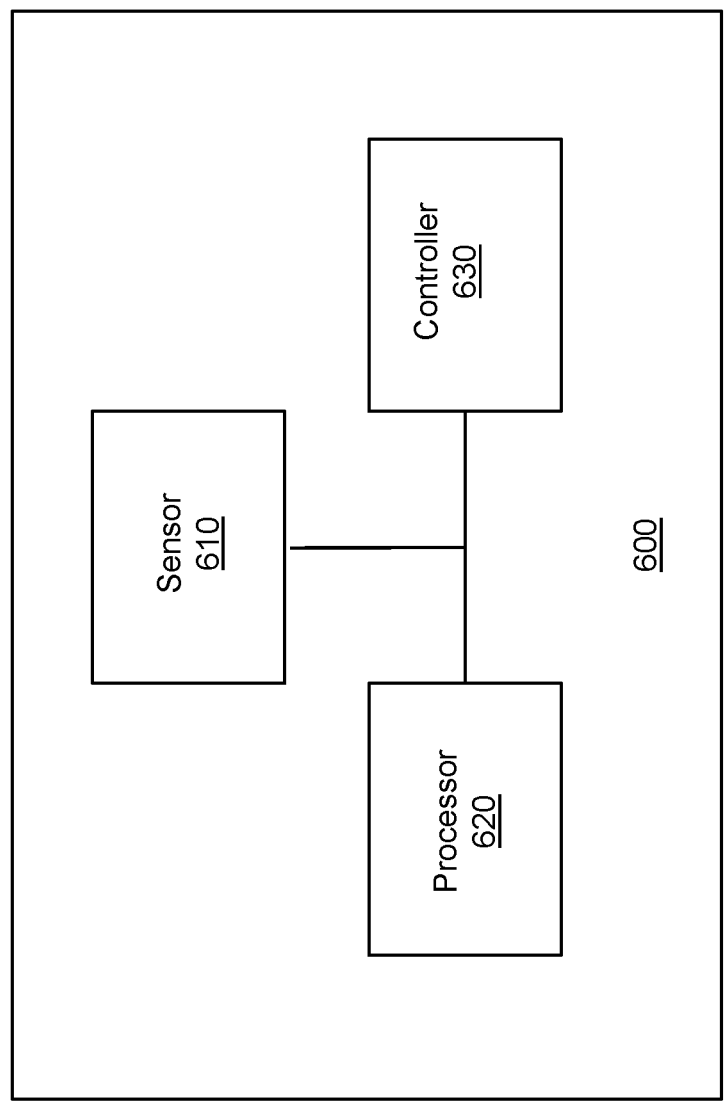
FIG. 6 illustrates a system for estimating a body temperature of an individual according to an embodiment of the invention.

FIG. 6 illustrates a system 600 for estimating a body temperature of an individual according to an embodiment of the invention. A sensor(s) 610 in a measurement device can be configured to measure physiological data of the individual (e.g., heart rate, skin temperature, activity data). For example, the physiological data includes activity data including running speed of the individual in miles per hour as detected by GPS or a pedometer. In another example, the physiological data includes an activity score of the individual (e.g., low, moderate, high, and very high), which is calculated by a processor using data obtained by heart rate monitor, GPS, pedometer, piezoelectric sensor, or other sensor on the individual. The activity score can also be manually input into the system by the individual, medical professional, or other user.

A processor 620 can receive the measured physiological data from the sensor(s) 610 and environmental data (e.g., ambient temperature, humidity) from an online resource. In at least one embodiment, the system 600 includes a second sensor in the measurement device to measure the environmental data instead of retrieving information from a data source such as an online resource. In another embodiment, the system 600 includes or is in communication with a GPS device in the measurement device to determine the location of the sensor 610, where the processor 620 queries an online resource with the location of the sensor to retrieve the environmental data. As used herein the term "processor" includes a computer hardware device connected to the sensor 610, such as, for example, a CPU, integrated circuit, or microprocessor. As used herein, the term "connected" includes operationally connected, logically connected, in communication with, physically or wirelessly connected, engaged, coupled, contacts, linked, affixed, and attached.

The processor 620 can input the physiological data and the environmental data into a model; and the model can generate an estimated core body temperature and an estimated physiological condition based on the physiological data and the environmental data. As discussed more fully above, the model includes a physiological mathematical model having a first equation that relates physical activity to heart rate, a second equation that relates heart rate to core body temperature, and a third equation that relates core body temperature to skin temperature.

The processor 620 can compare the estimated physiological condition (e.g., estimated heart rate, estimated skin temperature) to a measured physiological condition in the physiological data (e.g., measured heart rate, measured skin temperature). The model can use the physiological data and the environmental data to learn a physiological response of the individual and automatically adjusts the at least one parameter in the model to produce an individualized model.

More specifically, a controller 630 can modify one or more parameters in the model when the difference between the estimated physiological condition and the measured physiological condition is above a threshold. As used herein the term "controller" includes a computer hardware device connected to the processor 620, such as, for example, a CPU, integrated circuit, or microprocessor. The controller 630 can modify a rate constant for the heart rate signal ($\alpha_1$), a thermoregulatory rate constant for the core temperature signal ($\alpha_2$), a rate of convective heat loss/gain from the skin to the environment ($\alpha_3$), a rate of heat loss to the environment due to sweat evaporation ($\alpha_4$), a gain in heart rate due to physical activity ($\beta$), a rate of heat gain due to metabolic activity ($\gamma_1$), and/or a rate of heat loss/gain from the core to the skin ($\gamma_2$).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium is a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
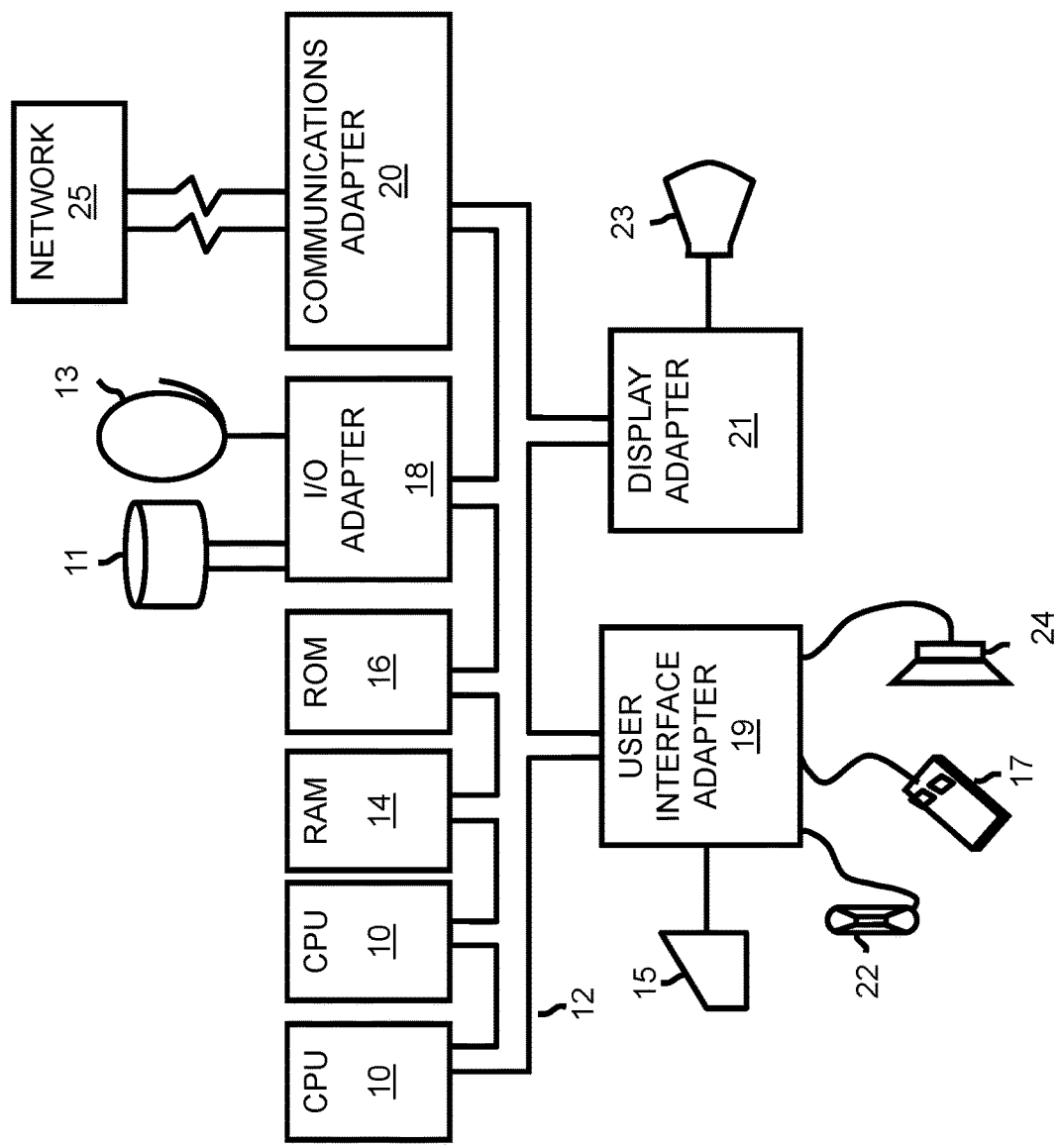
FIG. 7 illustrates a computer program product for estimating a body temperature of an individual according to an embodiment of the invention.

Referring now to FIG. 7, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

INDUSTRIAL APPLICABILITY

A system and method of estimating a body temperature of an individual is provided. The provided systems and methods are particularly suited for receiving environmental and physiological data from a sensor, and inputting the data into a model, where the model generates an estimated body temperature and an estimated physiological condition based on the data. The estimated physiological condition is compared to a measured physiological condition in the physiological data. One or more parameters in the model are modified when the difference between the estimated physiological condition and the measured physiological condition is above a threshold.

REFERENCES

[1] Ozaki T. The local linearization filter with application to nonlinear system identifications. *Proc first US/Japan Conf Frontiers Stat Modeling: An Informational Approach*, Springer, p. 217-240, 1994.
[2] Chen C-T. *Linear System Theory and Design*. 3$^{rd}$ ed. Oxford, N.Y.: Oxford University Press, 1999.
[3] Bulut Y, Vines-Cavanaugh D, Bernal D. Process and measurement noise estimation for Kalman filtering. *Structural Dynamics, Conf Proc Soc Exp Mech Series* 3: 375-386, 2011.

What is claimed is:

1. A method of estimating a body temperature of an individual and continual customization of a model for estimating the body temperature during performance of the method, said method comprising:
receiving with a processor a heart rate of the individual, a skin temperature of the individual, and activity data of the individual from at least one sensor;
receiving with the processor an ambient temperature and a humidity;
inputting the received activity data of the individual, the received ambient temperature, and the received humidity into the model operating on the processor and the model including a Kalman filter and a physiological model, wherein the physiological model generates an estimated heart rate based on the received activity data and an estimated skin temperature based on a skin temperature vapor pressure and a vapor pressure for a heat index for the received ambient temperature and the received humidity to account for a heat transfer from a skin of the individual to an environment in which the individual is present;
modifying by a controller using the Kalman filter at least one parameter in the physiological model based on a first error between the estimated heart rate and the received heart rate and/or a second error between the estimated skin temperature and the received skin temperature; and
estimating with the physiological model the body temperature reflecting a heat balance of the individual where the physiological model uses the at least one parameter that has been modified by the Kalman filter, and
wherein modifying at least one parameter customizes the physiological model to the individual by adapting to continual physiological changes in the individual.

2. The method according to claim 1, further comprising:
receiving a 3-D body acceleration of the individual from a wearable measuring device;
mapping the 3-D body acceleration into metabolic equivalent units to determine an activity score of the individual where the activity data includes the activity score.

3. The method according to claim 1, wherein the physiological model uses the following parameters:
a rate constant for heart rate;
a thermoregulatory rate constant;
a rate of convective heat loss/gain from a skin compartment to the environment;
a rate of heat loss to the environment due to sweat evaporation;
a rate of heat gain due to metabolic activity; and
a rate of heat loss/gain from the body temperature to the skin compartment.

4. The method according to claim 1, wherein the physiological mathematical model and the Kalman filter feed information to one another to learn a response for the individual to environmental and exertional heat stresses.

5. The method according to claim 1, wherein said receiving of the ambient temperature and the humidity includes:
determining a location of the sensor with a global positioning system (GPS) device; and
querying an online resource with the location of the sensor to retrieve the ambient temperature and the humidity.

6. The method according to claim 1, further comprising sending data from the at least one sensor to an external computing device, wherein the processor and the controller are on the external computing device.

7. The method according to claim 1, further comprising predicting a future body temperature of the individual using an autoregressive model based on the estimated body temperature and at least one additional estimated body temperature, the at least one estimated body temperature being generated after said modifying of at least one parameter in the model.

8. The method according to claim 1, wherein
estimating the body temperature with the physiological model uses the estimated heart rate and the estimated skin temperature; and
receiving the heart rate, the skin temperature, activity data, the ambient temperature, and the humidity; inputting; comparing; modifying; and estimating are repeated at predetermined intervals.

9. The method according to claim 1, wherein the Kalman filter modifies at least one parameter to reduce the first error and/or the second error when estimating a future heart rate and/or a future skin temperature.

10. A system for estimating a body temperature of an individual, said system comprising:

at least one physiological sensor configured to measure physiological data including physical activity, a heart rate, and a skin temperature;

at least one environmental sensor configured to measure environmental data;

a processor connected to said at least one physiological sensor and said at least one environmental sensor, said processor inputs the physiological data and the environmental data into a model configured to operate on said processor, wherein the model generates two estimated physiological conditions based on the physical activity and/or the environmental data, said processor compares at least one of the estimated physiological conditions to the respective measured physiological condition in the physiological data to find at least one error; and a controller in communication with said processor, said controller modifies at least one parameter in the model with a Kalman filter included in the model based on the at least one error to minimize the at least one error in a future estimation of that at least one physiological condition, and wherein the model further includes a physiological mathematical model using a plurality of parameters in:

a first equation that relates the physical activity to an estimated heart rate as one of the estimated physiological conditions using a rate constant for heart rate and a gain heart rate due to the physical activity, a second equation that relates the heart rate to an estimated body temperature using a thermoregulatory rate constant, a rate of heat gain due to metabolic activity with the estimated heart rate, a rate of heat loss/gain from core to skin with a first temperature gradient, and a third equation that relates the body temperature to an estimated skin temperature as another estimated physiological condition using a rate of convective heat loss/gain from the skin to the environment with a second temperature gradient, a rate of heat loss to the environment due to sweat evaporation, and the rate of heat loss/gain from the core to the skin with the first temperature gradient; and wherein said processor is configured to produce the estimated body temperature after the controller modifies at least one parameter in the physiological mathematical model using the second equation.

11. The system according to claim 10, wherein the model uses the physiological data and the environmental data to learn a physiological response of the individual and automatically adjusts with the Kalman filter the at least one parameter in the physiological mathematical model to produce an individualized model.

12. The system according to claim 10, wherein
the physical activity data of the individual includes an activity score of the individual,
said at least one sensor includes a third sensor, said third sensor configured to measure a 3-D body acceleration of the individual,
wherein said processor is configured to map the 3-D body acceleration into metabolic equivalent units to determine the activity score of the individual.

13. The system according to claim 10, wherein the measured heart rate and the measured skin temperature are used to customize the model to the individual based on an output of the Kalman filter.

14. The system according to claim 10, wherein the physiological mathematical model parameters include:
the thermoregulatory rate constant;
the rate of convective heat loss/gain;
the rate of heat loss to an environment due to sweat evaporation;
the gain in heart rate due to physical activity;
the rate of heat gain due to metabolic activity; and
the rate of heat loss/gain from the estimated body temperature to the skin compartment, and
wherein the model parameters are internal to the model and are distinct from the measured physiological data and the measured environmental data that are inputted into the model.

15. The system according to claim 10, wherein the model includes the physiological mathematical model and the Kalman filter that feed information to one another to learn a response for the individual to environmental and exertional heat stresses.

16. The system according to claim 10, further comprising a communications device connected to said at least one physiological sensor, said communications device configured to send data from said at least one physiological sensor and said at least one environmental sensor to an external computing device, wherein said processor and said controller are on said external computing device.

17. The system according to claim 10, wherein said processor is configured to predict with an autoregressive model a future body temperature of the individual based on the estimated body temperature and at least one additional estimated body temperature, the at least one estimated body temperature being generated after said controller modifies of at least one parameter in the model.

18. A method of estimating a body temperature of an individual, said method comprising:
receiving physiological data from at least one sensor, the physiological data including at least one of a heart rate of the individual, a skin temperature of the individual, and activity data of the individual, wherein the activity data of the individual includes at least one of a running speed of the individual and an activity score of the individual;
receiving environmental data, the environmental data including at least one of ambient temperature and humidity;
inputting the physiological data and the environmental data into a model, wherein the model generates an estimated body temperature and an estimated physiological condition based on the physiological data and the environmental data, wherein the model includes a physiological mathematical model including at least one of:
a first equation that relates physical activity to heart rate, wherein the first equation includes:

$$\frac{d\Delta H_R}{dt} = -\alpha_1 \Delta H_R + \beta A_C^4$$

where $\Delta H_R$ represents a change in heart rate from an initial heart rate $H_{R0}$, $H_R$ represents a current heart rate, dt represents a change in time, $\alpha_1$ represents a rate constant for $H_R$, $\beta$ represents a gain in heart rate due to physical activity, and $A_C$ represents an activity level,
a second equation that relates heart rate to core body temperature, and
a third equation that relates core body temperature to skin temperature;

comparing by a processor the estimated physiological condition to a measured physiological condition in the physiological data to find a difference; and modifying by a controller at least one parameter in the model when the difference between the estimated physiological condition and the measured physiological condition is above a threshold.

19. The method according to claim 18, wherein the second equation includes:

$$\frac{d\Delta T_C}{dt} = -\alpha_2 \Delta T_C + \gamma_1 \Delta H_R - \gamma_2(T_C - T_S)$$

where $\Delta T_C = T_C - T_{C0}$ with $T_{C0}$ representing an initial core temperature; $T_C$ and $T_S$ represent current core and skin temperatures, respectively; dt represents a change in time; $\Delta H_R$ represents a change in heart rate from an initial heart rate $H_{R0}$; $\alpha_2$ denotes a thermoregulatory rate constant of $T_C$, $\gamma_1$ denotes a rate of heat gain due to metabolic activity ($H_R$); and $\gamma_2$ represents a rate of heat loss/gain from a core to a skin.

20. The method according to claim 18, wherein the third equation includes:

$$\frac{d\Delta T_S}{dt} = -\alpha_3(T_S - T_A) - \alpha_4(P_S - P_A) + \gamma_2(T_C - T_S)$$

where $\Delta T_S = T_S - T_{S0}$ with $T_{S0}$ representing initial skin temperature and $T_C$ and $T_S$ represent current core and skin temperatures, respectively; dt represents a change in time; $P_S$ denotes a vapor pressure of water for $T_S$; $P_A$ represents a vapor pressure of water due to a heat index perceived by humans at a given ambient temperature $T_A$ and relative humidity $R_H$; $\gamma_2$ represents a rate of heat loss/gain from a core to a skin; $\alpha_3$ represents a rate of convective heat loss/gain from the skin to an environment; and $\alpha_4$ represents a rate of heat loss to the environment due to sweat evaporation.

* * * * *